United States Patent
He et al.

(10) Patent No.: US 11,896,309 B2
(45) Date of Patent: Feb. 13, 2024

(54) RETINA IMAGING SYSTEM BASED ON THE COMMON BEAM SCANNING

(71) Applicant: Suzhou Institute of Biomedical Engineering and Technology, Chinese Academy of Sciences, Jiangsu (CN)

(72) Inventors: Yi He, Jiangsu (CN); Guohua Shi, Jiangsu (CN); Feng Gao, Jiangsu (CN); Wen Kong, Jiangsu (CN); Lina Xing, Jiangsu (CN); Wanyue Li, Jiangsu (CN); Jing Wang, Jiangsu (CN); Xin Zhang, Jiangsu (CN)

(73) Assignee: SUZHOU INSTITUTE OF BIOMEDICAL ENGINEERING AND TECHNOLOGY, CHINESE ACADEMY OF SCIENCES, Suzhou (CN)

( * ) Notice: Subject to any disclaimer, the term of this patent is extended or adjusted under 35 U.S.C. 154(b) by 847 days.

(21) Appl. No.: 16/971,570

(22) PCT Filed: Oct. 22, 2019

(86) PCT No.: PCT/CN2019/112521
§ 371 (c)(1),
(2) Date: Aug. 20, 2020

(87) PCT Pub. No.: WO2021/046973
PCT Pub. Date: Mar. 18, 2021

(65) Prior Publication Data
US 2023/0094588 A1    Mar. 30, 2023

(30) Foreign Application Priority Data
Sep. 9, 2019   (CN) .......................... 201910865740.4

(51) Int. Cl.
A61B 3/10 (2006.01)
A61B 3/12 (2006.01)
A61B 3/15 (2006.01)

(52) U.S. Cl.
CPC .......... *A61B 3/1025* (2013.01); *A61B 3/1015* (2013.01); *A61B 3/12* (2013.01); *A61B 3/152* (2013.01)

(58) Field of Classification Search
CPC ....... A61B 3/1025; A61B 3/1015; A61B 3/12; A61B 3/152; A61B 3/112; A61B 3/113;
(Continued)

(56) References Cited

U.S. PATENT DOCUMENTS

| 9,867,538 B2 | 1/2018 | Nozato et al. |
| 2007/0252951 A1 | 11/2007 | Hammer et al. |

(Continued)

FOREIGN PATENT DOCUMENTS

| CN | 101862178 A | 10/2010 |
| CN | 103054550 A | 4/2013 |

(Continued)

OTHER PUBLICATIONS

Webb et al., "Confocal scanning laser ophthalmoscope," Applied Optics, April 15, 1987, vol. 26, No. 8, 8 pages.
(Continued)

*Primary Examiner* — Travis S Fissel
(74) *Attorney, Agent, or Firm* — Crowell & Moring LLP (57) ABSTRACT

A common beam scanning retinal imaging system comprises: a light source module (1), an adaptive optics module (2), a beam scanning module (3), a small field-of-view relay module (5), a large field-of-view relay module (6), a sight beacon module (9), a pupil monitoring module (7), a detection module (8), a control module (10) and an output module (11). The system can perform real-time correction of human
(Continued)

eye aberration by adaptive optics technology, and realize the confocal scanning imaging function in a large field of view and the adaptive optics high-resolution imaging function in a small field of view simultaneously by the common beam synchronous scanning configuration combined with the two relay optical path structures for both the small field of view and the large field of view. The system can not only observe disease lesions in a wide range on the retina by the large field-of-view imaging, but also observe fine structures of the lesions by the small field-of-view high-resolution imaging. A variety of imaging images are acquired by common path optical beam scanning to meet the needs of different application scenes, which greatly expands the application range of the existing confocal imaging equipment.

9 Claims, 3 Drawing Sheets

(58) Field of Classification Search
CPC ....... A61B 3/14; A61B 3/0091; A61B 3/1035; A61B 3/107; A61B 3/1173; A61B 3/1208; A61B 3/1216; A61B 3/1225; A61B 3/13; A61B 3/15; A61B 5/0073; G02B 21/0012; G02B 21/0028; G02B 21/0032; G02B 21/008; G02B 21/18; G02B 21/0036; G02B 21/0044; G02B 21/0048; G02B 21/025; G02B 21/04
USPC ................ 351/206, 208, 209, 210, 216, 236
See application file for complete search history.

(56) References Cited

U.S. PATENT DOCUMENTS

| | | |
|---|---|---|
| 2010/0277692 A1 | 11/2010 | Mukai et al. |
| 2013/0215385 A1 | 8/2013 | Hirose |
| 2015/0077710 A1 | 3/2015 | Saito et al. |
| 2016/0317030 A1* | 11/2016 | He ..................... G02B 27/0068 |
| 2017/0265742 A1 | 9/2017 | Nozato et al. |
| 2020/0178797 A1* | 6/2020 | Levecq ..................... A61B 3/14 |

FOREIGN PATENT DOCUMENTS

| | | |
|---|---|---|
| CN | 104783755 A | 7/2015 |
| FR | 3065365 A1 | 10/2018 |
| JP | 2016209571 | 12/2016 |
| JP | 2016214466 A | 12/2016 |
| JP | 2017170141 | 9/2017 |
| WO | WO2018197288 A1 | 11/2018 |

OTHER PUBLICATIONS

International Search Report and Written Opinion with concise English translation regarding PCT/CN2019/112521 dated Jun. 15, 2020, 12 pages.
Japanese Office Action with English translation regarding JP2020544628 dated Dec. 3, 2021.
Korean Office Action with English translation regarding KR 091905946 dated Nov. 23, 2021.
European Search Regort regarding EP19915588 dated May 31, 2021.
First European Office Action regarding EP 19 9155888 dated Jul. 22, 2021.
Communication pursuant to Article 94(3) EPC from the European Patent Office regarding Application No. 19 915 588.8 dated Jun. 9, 2023, 5 pages.

\* cited by examiner

RETINA IMAGING SYSTEM BASED ON THE COMMON BEAM SCANNING

CROSS REFERENCE TO RELATED APPLICATION

The present application claims priority of Chinese Patent Application No. 201910865740.4 filed on Sep. 9, 2019 and entitled "common beam scanning retinal imaging system", the entire contents of which are incorporated herein by reference.

TECHNICAL FIELD

The present application relates to the field of optical imaging technology, and specifically relates to a common beam scanning retinal imaging system.

BACKGROUND OF THE INVENTION

The traditional confocal scanning technology was developed into a mature confocal scanning laser imaging equipment in 1987 (Webb R, Hughes G, Delori F. Confocal scanning laser ophthalmoscope. Applied optics. 1987; 26(8): 1492-9), and is widely used in retinal imaging and can achieve large field-of-view in-vivo imaging of fundus retina. However, since the eyeball is a complex optical system, and even an eye without a refractive error inevitably has optical aberration. In particular, in order to obtain high resolution at a large value of optical aperture, higher resolution at the diffraction limit may be obtained with a larger pupil according to optical theory, but a larger pupil brings more aberration of the human eye which greatly limits the actual resolution. Traditional confocal scanning laser ophthalmoscopes can usually obtain images with a large field of view of the eye fundus over 10 degrees, but it is very difficult for them to distinguish blood vessels below 20 microns, let alone observe fine structures such as visual cells.

In the 1890s, with the introduction of adaptive optics technology into the imaging of fundus retina, correction devices such as an adaptive optics deformable mirror are used to correct aberration of human eye well, so as to obtain high resolution at the diffraction limit, making it possible for the first time to observe retinal micro-vessels and visual cells in vivo. The patent literature with the patent number of ZL201010197028.0 proposes a retinal imaging device based on adaptive optics technology, wherein the device performs two-dimensional synchronous scanning of the retinal plane by using two independent scanning mirrors, so as to realize confocal scanning imaging and realize functions of high-resolution imaging. However, the device can only achieve high-resolution imaging of the human eye with a maximum field of view of 3 degrees. Due to the limitation of halo region in adaptive optical aberration correction, adaptive optics often makes a compromise in the field of view of imaging while realizing high-resolution imaging, and can only realize imaging in a small field of view within 3 degrees.

In summary, it can be seen that the existing confocal scanning laser ophthalmoscopes having a large field of view of imaging do not have sufficient resolution to observe the fine structures of the retina; and the existing confocal scanning laser ophthalmoscopes combined with the adaptive optics can observe the fine structures of the retina, but have a small field of view of imaging, which makes it impossible to observe the lesions in a larger field of view.

SUMMARY

The technical problem to be solved by the present application is to provide a common beam scanning retinal imaging system directed to overcome the above-mentioned deficiencies in the prior art.

In order to solve the above-mentioned technical problem, the present application adopts the following technical solutions:

A common beam scanning retinal imaging system comprises: a light source module, an adaptive optics module, a beam scanning module, a small field-of-view relay module, a large field-of-view relay module, a sight beacon module, a pupil monitoring module, a detection module, a control module and an output module; the light source module is configured to emit a parallel light beam with at least two different wavelengths, wherein the parallel light beam irradiates a human eye after going through the adaptive optics module, the beam scanning module, and the small field-of-view relay module or the large field-of-view relay module sequentially, imaging light that is scattered by the human eye and carries aberration information of the human eye and light intensity information returns along an original optical path of the parallel light beam and reaches the adaptive optics module and the detection module; the adaptive optics module is configured to receive the imaging light carrying the aberration information of the human eye, and perform real-time measurement and correction of wavefront aberration; the beam scanning module includes a biaxial scanning mirror which is connected to the adaptive optics module through a first transmissive or reflective telescope along an incident end of the optical path and is connected to the small field-of-view relay module or the large field-of-view relay module through a second transmissive or reflective telescope along an exit end of the optical path, so as to achieve a small field-of-view high-resolution imaging and a large field-of-view low-resolution imaging, respectively; the small field-of-view relay module is configured as a beam expanding telescope, and the large field-of-view relay module is configured as a beam contracting telescope; the sight beacon module is configured to guide and fix a sight beacon of the human eye; the pupil monitoring module is configured to align and monitor a pupil of the human eye; the detection module is configured to receive the returning imaging light of the human eye, convert the imaging light into an electrical signal, and transmit the electrical signal to the control module; and the output module is configured to connect to the control module, and display and store imaging images of the human eye.

Optionally, the system further comprises a dichroic beam splitter module including a first dichroic beam splitter, a second dichroic beam splitter, a third dichroic beam splitter and a fourth dichroic beam splitter arranged successively along an incident optical path; the light source module includes a light source, a collimator and a first beam splitter arranged successively along the incident optical path, and is configured to output a parallel light beam to the adaptive optics module, wherein the light emitted by the light source passes through the collimator, and is then partially transmitted through the first beam splitter to enter the adaptive optics module; the adaptive optics module includes a wavefront corrector, a second beam splitter, an optical filter and a wavefront sensor arranged successively along a returning optical path of human eye imaging, and is connected to the beam scanning module; wherein the parallel light beam outputted by the light source module is reflected to the beam scanning module by the wavefront corrector; wherein the returning imaging light carrying the aberration information of the human eye and the light intensity information exits from the beam scanning module and is reflected to the first beam splitter by the wavefront corrector, one part of the light reflected by the first beam splitter is then reflected by the second beam splitter, passes through the optical filter, and then reaches the wavefront sensor, so as to realize measurement of wavefront aberration, and the other part of the light reflected by the first beam splitter is transmitted through the second beam splitter and enters the detection module; and the wavefront sensor is configured to receive an imaging light beam containing the aberration information of the human eye and transmit the aberration information to the control module, the control module is configured to perform wavefront calculation, detect wavefront aberration, obtain a wavefront control voltage and output the wavefront control voltage to the wavefront corrector, and the wavefront corrector is configured to correct the wavefront aberration.

Optionally, the detection module includes a fifth dichroic beam splitter, a first detection optical path and a second detection optical path, wherein the fifth dichroic beam splitter is configured to transmit one part of the received light to the first detection optical path and simultaneously reflect the other part of the received light to the second detection optical path; the first detection optical path includes a first collection lens, a first pinhole and a first detector, and the second detection optical path includes a second collection lens, a second pinhole and a second detector; wherein one part of the returning imaging light beam carrying the light intensity information of the human eye is transmitted through the fifth dichroic beam splitter and outputted to the first collection lens, passes through the first pinhole and reaches the first detector, so as to obtain a retinal imaging image; wherein the other part of the returning imaging light beam carrying the light intensity information of the human eye is reflected by the fifth dichroic beam splitter and outputted to the second collection lens, passes through the second pinhole and reaches the second detector, so as to obtain another retinal imaging image; the beam scanning module includes a first transmissive or reflective telescope, a biaxial scanning mirror and a second transmissive or reflective telescope arranged successively along the incident optical path, wherein the biaxial scanning mirror is configured to be driven by a periodic voltage outputted from the control module to perform horizontal and vertical two-dimensional scanning of the retinal plane.

Optionally, the sight beacon module includes an LED array, a sight beacon lens, and a first planar reflection mirror, wherein the light emitted by any one of LED beads in the LED array after being lit by the control module propagates through the sight beacon lens, is reflected by the first planar reflection mirror, is reflected by the first dichroic beam splitter, and is sequentially transmitted through the second dichroic beam splitter, the third dichroic beam splitter and the fourth dichroic beam splitter, and then reaches the human eye, so as to allow the human eye to gaze at the luminous LED bead to achieve sight fixation; the pupil monitoring module includes a ring-shaped LED array, an imaging lens, and an area-array detector, wherein the light emitted by the ring-shaped LED array illuminates the pupil of the human eye, and is reflected by the pupil of the human eye, passes through a hollow part of the ring-shaped LED array, is transmitted through the fourth dichroic beam splitter, is reflected by the third dichroic beam splitter, and is finally focused by the imaging lens to the area-array detector for pupil imaging; and the area-array detector is configured to convert the received light signal into an electrical signal and then output the electrical signal to the control module; the control module is configured to obtain a pupil imaging image and finally output the pupil imaging image to the output module for display and storage.

Optionally, the small field-of-view relay module includes a transmissive telescope comprising a first lens and a second lens and having a magnification greater than 1, or a reflective telescope comprising a first spherical reflector and a second spherical reflector and having a magnification greater than 1; the small field-of-view relay module further includes a first focusing mechanism disposed between the two lenses or spherical reflectors of the telescope, wherein the first focusing mechanism includes two orthogonal planar reflection mirrors and is configured to reciprocate along a central optical axis of the telescope to compensate for a refractive error of the human eye; the large field-of-view relay module includes a transmissive telescope comprising a third lens and a fourth lens and having a magnification less than 1, or a reflective telescope comprising a third spherical reflector and a fourth spherical reflector and having a magnification less than 1; the large field-of-view relay module further includes a second focusing mechanism disposed between the two lenses or spherical reflectors of the telescope, wherein the second focusing mechanism includes two orthogonal planar reflection mirrors, and is configured to reciprocate along a central optical axis of the telescope to compensate for a refractive error of the human eye.

Optionally, the small field-of-view high-resolution imaging is performed by the following process: the light beam emitted by the light source module goes through the wavefront corrector of the adaptive optics module and the beam scanning module, and is reflected by the first dichroic beam splitter to enter the small field-of-view relay module, then exits from the small field-of-view relay module and is reflected by the second dichroic beam splitter, is transmitted through the third dichroic beam splitter and the fourth dichroic beam splitter, passes through the hollow part of the ring-shaped LED array to reach the human eye, and is focused on a point on the fundus retina by the optical system of the human eye; the incident light beam is scattered by the fundus retina to form a scattered imaging light beam carrying aberration information of the human eye and light intensity information at the point on the fundus retina; the scattered imaging light beam returns along the original optical path and exits from the beam scanning module, and is then reflected by the wavefront corrector to the first beam splitter; the first beam splitter reflects the light beam to the second beam splitter, one part of the light reflected by the first beam splitter is reflected by the second beam splitter to enter the wavefront sensor; the wavefront sensor transmits the received aberration information of the human eye to the control module; the control module restores the wavefront aberration and calculates an aberration correction voltage, and then transmits the aberration correction voltage to the wavefront corrector to perform real-time correction of human eye aberration; at the same time, the other part of the light reflected by the first beam splitter is transmitted through the second beam splitter, and is then transmitted totally through the fifth dichroic beam splitter, then passes through the first collection lens and the first pinhole, and finally reaches the first detector; the first detector converts the received light signal of the fundus retina into an electrical signal and outputs the electrical signal to the control module; the control module performs signal synchronization processing, samples the electrical signal to reconstruct an imaging image of the retina with a small field of view and high resolution, which is then displayed and stored by the output module; and the large field-of-view low-resolution imaging is performed by the following process:

The light beam emitted by the light source module goes through the wavefront corrector of the adaptive optics module and the beam scanning module, is transmitted through the first dichroic beam splitter and the second dichroic beam splitter, and is reflected by the third dichroic beam splitter to enter the large field-of-view relay module, then exits from the large field-of-view relay module and is reflected by the fourth dichroic beam splitter, passes through the hollow part of the ring-shaped LED array to reach the human eye, and is focused on a point on the fundus retina by the optical system of the human eye; the incident light beam is scattered by the fundus retina to form a scattered imaging light beam carrying light intensity information at the point on the fundus retina; the scattered imaging light beam returns along the original optical path and exits from the beam scanning module, and is then reflected by the wavefront corrector to the first beam splitter; the first beam splitter reflects the light beam to the second beam splitter, the light reflected by the first beam splitter is transmitted through the second beam splitter, and is then reflected totally by the fifth dichroic beam splitter, then passes through the second collection lens and the second pinhole, and finally reaches the second detector; the second detector converts the received light signal of the fundus retina into an electrical signal and output the electrical signal to the control module; the control module performs signal synchronization processing, samples the electrical signal to reconstruct an imaging image of the retina with a large field of view and low resolution, which is then displayed and stored by the output module.

Optionally, the light source module includes at least two light sources, wherein the lights emitted from the at least two light sources are coupled by an optical-fiber coupler and go into a collimator to be collimated into a parallel light beam, or wherein the lights emitted from the at least two light sources are collimated by corresponding collimators respectively into parallel light beams which are then combined by a dichroic beam splitter to enter the optical path; the light emitted by the light source module includes light with a wavelength $\lambda_1$ of 600 nm-850 nm and light with a wavelength $\lambda_2$ of 900 nm-1000 nm, wherein the light with the wavelength $\lambda_1$ is used for the small field-of-view high-resolution imaging, and the light with the wavelength $\lambda_2$ is used for the large field-of-view low-resolution imaging; the ring-shaped LED array includes at least three LED beads arranged along a ring at equal intervals, the hollow part of the ring-shaped LED array has a light-transmitting aperture no less than the diameter of the imaging light beam; the wavelength of the light emitted by the LED beads is $\lambda_3$ which is greater than 1000 nm; the LED array of the sight beacon module includes LED beads arranged in an equally spaced array and emitting light with a wavelength $\lambda_4$ in a range of 380 nm-760 nm in the visible light band, and the difference between $\lambda_4$ and either of $\lambda_1$, $\lambda_2$ is at least 50 nm.

Optionally, the first dichroic beam splitter has a reflection effect on the lights with the wavelengths $\lambda_1$ and $\lambda_4$, and has a transmission effect on the light with the wavelength $\lambda_2$; the second dichroic beam splitter has a reflection effect on the light with the wavelength $\lambda_1$, and has a transmission effect on the lights with the wavelengths $\lambda_2$ and $\lambda_4$; the third dichroic beam splitter has a reflection effect on the lights with the wavelengths $\lambda_2$ and $\lambda_3$, and has a transmission effect on the lights with the wavelengths $\lambda_1$ and $\lambda_4$; and the fourth dichroic beam splitter has a reflection effect on the light with the wavelength $\lambda_2$ and has a transmission effect on the lights with the wavelengths $\lambda_1$, $\lambda_3$, and $\lambda_4$.

Optionally, the wavefront sensor in the adaptive optics module is selected from a microprism array Hartmann wavefront sensor, a microlens array Hartmann wavefront sensor, a quadrangular pyramid sensor and a curvature sensor; and the wavefront corrector is selected from a deformable reflection mirror, a liquid crystal spatial light modulator, a micromachined membrane deformable mirror, a micro-electromechanical deformable mirror, a double piezoelectric ceramic deformable mirror and a liquid deformable mirror;

the second dichroic beam splitter splits the imaging light beam reflected from the first beam splitter by reflecting 5% of the light to pass through the optical filter and enter the wavefront sensor for wavefront aberration measurement and transmitting the remaining 95% of the light to the fifth dichroic beam splitter; the optical filter is a broadband filter whose transmission wavelength band satisfies the selected wavelength $\lambda_1$ for the small field-of-view high-resolution imaging, or is a combination of multiple narrowband filters whose combined transmission wavelength band satisfies the selected wavelength $\lambda_1$ for the small field-of-view high-resolution imaging; and wherein the imaging light beam of the selected wavelength $\lambda_2$ for the large field-of-view low-resolution imaging is completely blocked by the optical filter and does not enter the wavefront sensor; the wavefront aberration detected by the wavefront sensor is processed by the control module, and the obtained wavefront control voltage is outputted to the wavefront corrector, so as to correct the wavefront aberration.

Optionally, the biaxial scanning mirror is a two-dimensional scanning mirror for realizing the horizontal and vertical scanning of the light beam, or is a combination of two one-dimensional scanning mirrors wherein scanning directions of the two scanning mirrors are set to be orthogonal to each other for realizing horizontal scanning and vertical scanning of the light beam respectively, and the two scanning mirrors are connected by a transmissive telescope or a reflective telescope to achieve a matching of light pupils; the first transmissive or reflective telescope is configured to connect the wavefront corrector to the biaxial scanning mirror to achieve a matching of light pupils, and has a magnification equal to a ratio of the light-transmitting aperture of the biaxial scanning mirror to the light-transmitting aperture of the wavefront corrector; and the second transmissive or reflective telescope is configured to conjugatively transmit the exiting light of the biaxial scanning mirror to the first dichroic beam splitter.

The present application has the following beneficial effects:

The common beam scanning retinal imaging system provided by the present application can simultaneously obtain large field-of-view low-resolution imaging images and small field-of-view high-resolution imaging images of the fundus retina by using only one set of scanning mechanism. The two types of imaging images are collected by a common optical path structure. Therefore, the two types of imaging images have the same center position and imaging speed, and the image characteristics thereof have good consistency, which is convenient for comparison processing and operation.

As compared with domestic and foreign technological achievements in the field of confocal scanning laser imaging, the present application can perform real-time correction of human eye aberration by adaptive optics technology, and realize the confocal scanning imaging function in a large field of view with a single-time large field-of-view imaging range of greater than 20 degrees and the adaptive optics high-resolution imaging function in a small field of view with a single-time small field-of-view imaging range of no more than 5 degrees simultaneously by the common beam synchronous scanning configuration combined with the two relay optical path structures for both the small field of view and the large field of view. The system can not only observe disease lesions in a wide range on the retina by the large field-of-view imaging, but also observe the fine structures of the lesions by the small field-of-view high-resolution imaging. A variety of imaging images are acquired by common path optical beam scanning to meet the needs of different application scenes, which greatly expands the application range of the existing confocal imaging equipment.

Wherein the reference numerals are: 1—light source module; 2—adaptive optics module; 3—beam scanning module; 5—small field-of-view relay module; 6—large field-of-view relay module; 7—pupil monitoring module; 8—detection module; 9—sight beacon module; 10—control module; 11—output module; 12—human eye; 101—light source; 102—collimator; 103—first beam splitter; 201—wavefront corrector; 202—second beam splitter; 203—optical filter; 204—wavefront sensor; 301—first transmissive or reflective telescope; 302—biaxial scanning mirror; 303—second transmissive or reflective telescope; 401—first dichroic beam splitter; 402—second dichroic beam splitter; 403—third dichroic beam splitter; 404—fourth dichroic beam splitter; 501—first lens or first spherical reflector; 502—first focusing mechanism; 503—second lens or second spherical reflector; 601—third lens or third spherical reflector; 602—second focusing mechanism; 603—fourth lens or fourth spherical reflector; 701—ring-shaped LED array; 702—imaging lens; 703—area-array detector; 800—fifth dichroic beam splitter; 801—first collection lens; 802—first pinhole; 803—first detector; 811—second collection lens; 812—second pinhole; 813—second detector; 901—LED array; 902—sight beacon lens; 903—first planar reflection mirror.

DETAILED DESCRIPTION

The present application will be further described in detail below with reference to the embodiments, so that a person skilled in the art can implement it according to the written description.

It should be understood that terms such as "have", "comprise' and "include" used herein are not intend to exclude the presence or addition of one or more other elements or combinations thereof.

Figure 1:
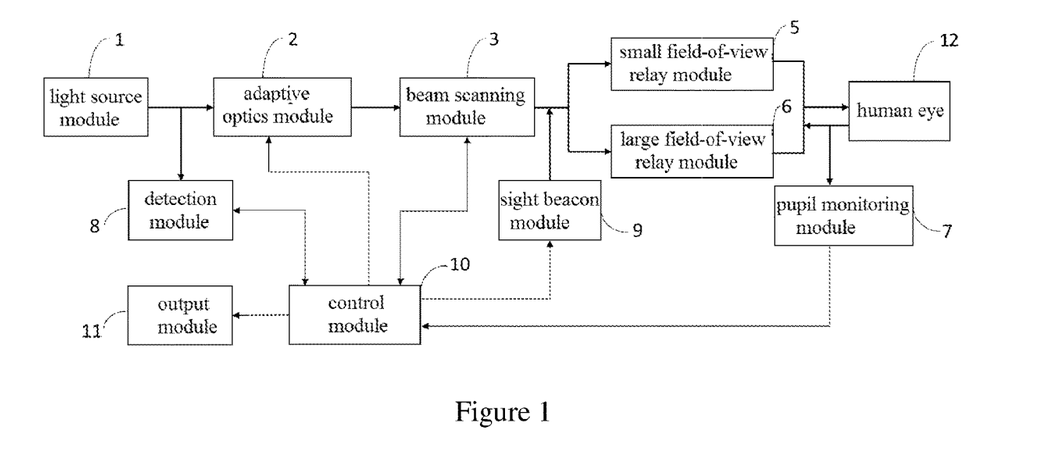
FIG. 1 is a schematic block diagram of the common beam scanning retinal imaging system of the present application.
Figure 2:
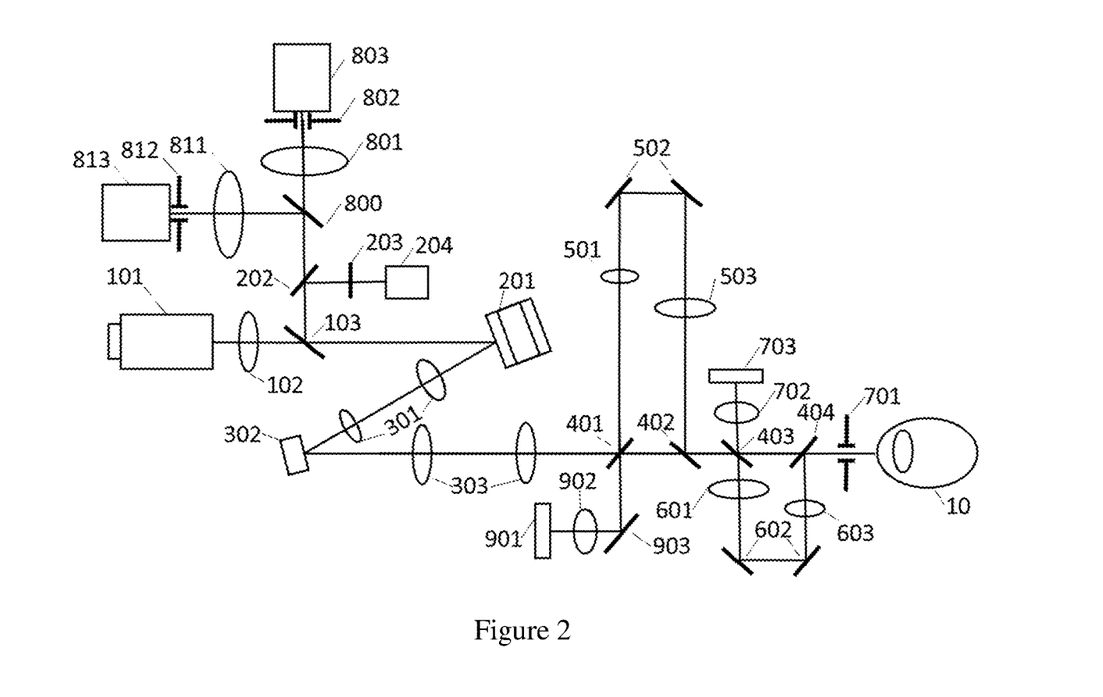
FIG. 2 is a diagram of an optical path structure of the common beam scanning retinal imaging system of the present application.

As shown in FIGS. 1-2, a common beam scanning retinal imaging system of the present embodiment includes: a light source module 1, an adaptive optics module 2, a beam scanning module 3, a small field-of-view relay module 5, a large field-of-view relay module 6, a sight beacon module 9, a pupil monitoring module 7, a detection module 8, a control module 10 and an output module 11.

The light source module 1 emits a parallel light beam with at least two different wavelengths. The parallel light beam irradiates a human eye 12 after going through the adaptive optics module 2, the beam scanning module 3, and the small field-of-view relay module 5 or the large field-of-view relay module 6 sequentially, imaging light that is scattered by the human eye 12 and carries aberration information of the human eye and light intensity information returns along an original optical path of the parallel light beam and reaches the adaptive optics module 2 and the detection module 8.

The adaptive optics module 2 receives the imaging light carrying the aberration information of the human eye, and performs real-time measurement and correction of wavefront aberration.

The beam scanning module 3 includes a biaxial scanning mirror 302 which is connected to the adaptive optics module 2 through a first transmissive or reflective telescope 301 along an incident end of the optical path and is connected to the small field-of-view relay module 5 or the large field-of-view relay module 6 through a second transmissive or reflective telescope 303 along an exit end of the optical path, so as to achieve a small field-of-view high-resolution imaging and a large field-of-view low-resolution imaging, respectively.

The small field-of-view relay module 5 is configured as a beam expanding telescope, and the large field-of-view relay module 6 is configured as a beam contracting telescope.

The sight beacon module 9 guides and fixes a sight beacon of the human eye.

The pupil monitoring module 7 aligns and monitors a pupil of the human eye.

The detection module 8 receives the returning imaging light of the human eye, converts the imaging light into an electrical signal, and transmits the electrical signal to the control module 10.

The output module 11 is configured to connect to the control module 10, and display and store imaging images of the human eye.

Wherein, the light source module 1 includes a light source 101, a collimator 102 and a first beam splitter 103 arranged successively along the incident optical path, and is configured to output a parallel light beam to the adaptive optics module 2, wherein the light emitted by the light source 101 passes through the collimator 102, and is then partially transmitted through the first beam splitter 103 to enter the adaptive optics module 2. The light source module 1 includes at least two light sources 101, wherein the lights emitted from the at least two light sources 101 are coupled by an optical-fiber coupler and goes into a collimator 102 to be collimated into a parallel light beam; or the lights emitted from the at least two light sources 101 are collimated by corresponding collimators 102 respectively into parallel light beams which are then combined by a dichroic beam splitter to enter the optical path.

In a preferred embodiment, the light emitted by the light source module 1 includes light with a wavelength $\lambda 1$ and light with a wavelength $\lambda 2$. The wavelength $\lambda 1$ is 600 nm-850 nm, optionally 670 nm, 730 nm, 795 nm and 830 nm, and more preferably 670 nm and 795 nm. The light with the wavelength $\lambda 1$ is used for small field-of-view high-resolution imaging. The wavelength λ2 is 900 nm-1000 nm. The light with the wavelength λ2 is used for large field-of-view low-resolution imaging.

In a preferred embodiment, the collimator 102 may be a single lens, an achromatic lens, an apochromatic lens, a combination of lenses or a parabolic mirror, and the collimator 102 is used to collimate the light beam emitted by the light source 101 into a parallel light beam. The reflective collimator RC12FC-P01 available from Thorlabs Company is used in this embodiment. The beam splitter is a broadband beam splitter with a transmittance-to-reflectance ratio of 20:80.

Wherein, the pupil monitoring module 7 includes a ring-shaped LED array 701, an imaging lens 702, and an area-array detector 703. The light emitted by the ring-shaped LED array 701 illuminates the pupil of the human eye, and is reflected by the pupil of the human eye, passes through a hollow part of the ring-shaped LED array 701, is transmitted through the fourth dichroic beam splitter 404, is reflected by the third dichroic beam splitter 403, and is finally focused by the imaging lens 702 to the area-array detector 703 for pupil imaging. The area-array detector 703 converts the received light signal into an electrical signal and then outputs the electrical signal to the control module 10. The control module 10 obtains a pupil imaging image and finally outputs the pupil imaging image to the output module 11 for display and storage.

In a preferred embodiment, the ring-shaped LED array 701 includes at least three LED beads arranged along a ring at equal intervals, the hollow part of the ring-shaped LED array has a light-transmitting aperture no less than the diameter of the imaging light beam; the wavelength of the light emitted by the LED beads is $\lambda_3$ which is greater than 1000 nm, optionally 1020 nm and 1310 nm, preferably 1020 nm.

Wherein, the sight beacon module 9 includes an LED array 901, a sight beacon lens 902, and a first planar reflection mirror 903. The light emitted by any one of LED beads in the LED array 901 after being lit by the control module 101 propagates through the sight beacon lens 902, is reflected by the first planar reflection mirror 903, is reflected by the first dichroic beam splitter 401, and is sequentially transmitted through the second dichroic beam splitter 402, the third dichroic beam splitter 403, the fourth dichroic beam splitter 404 and the hollow part of the ring-shaped LED array 701, and then reaches the human eye 12, so as to allow the human eye to gaze at the luminous LED bead to achieve sight fixation.

The LED array 901 includes LED beads arranged in an equally spaced array and emitting light with a wavelength $\lambda_4$, and the difference between $\lambda_4$ and either of $\lambda_1$, $\lambda_2$ is at least 50 nm.

Wherein, the adaptive optics module 2 includes a wavefront corrector 201, a second beam splitter 202, an optical filter 203 and a wavefront sensor 204 arranged successively along a returning optical path of human eye imaging, and is connected to the beam scanning module 3. The parallel light beam outputted by the light source module 1 is reflected to the beam scanning module 3 by the wavefront corrector 201. The returning imaging light carrying the aberration information of the human eye and the light intensity information exits from the beam scanning module 3 and is reflected to the first beam splitter 103 by the wavefront corrector 201, one part of the light reflected by the first beam splitter 103 is then reflected by the second beam splitter 202, passes through the optical filter 203, and then reaches the wavefront sensor 204, so as to realize measurement of wavefront aberration, and the other part of the light reflected by the first beam splitter 103 is transmitted through the second beam splitter 202 and enters the detection module 8.

In a preferred embodiment, the wavefront sensor 204 in the adaptive optics module 2 is selected from a microprism array Hartmann wavefront sensor 204, a microlens array Hartmann wavefront sensor 204, a quadrangular pyramid sensor and a curvature sensor; and the wavefront corrector 201 is selected from a deformable reflection mirror, a liquid crystal spatial light modulator, a micromachined membrane deformable mirror, a micro-electromechanical deformable mirror, a double piezoelectric ceramic deformable mirror and a liquid deformable mirror.

In a preferred embodiment, the second beam splitter 202 is a broadband beam splitter with a transmittance-to-reflectance ratio of 95:5. The second dichroic beam splitter 202 splits the imaging light beam reflected from the first beam splitter 103 by reflecting 5% of the light to pass through the optical filter 203 and enter the wavefront sensor 204 for wavefront aberration measurement and transmitting the remaining 95% of the light to the fifth dichroic beam splitter 800. The optical filter 203 is a broadband filter 203 whose transmission wavelength band satisfies the selected wavelength $\lambda_1$ for the small field-of-view high-resolution imaging, or is a combination of multiple narrowband filters whose combined transmission wavelength band satisfies the selected wavelength $\lambda_1$ for the small field-of-view high-resolution imaging; and wherein the imaging light beam with the selected wavelength $\lambda_2$ for the large field-of-view low-resolution imaging is completely blocked by the optical filter 203 and does not enter the wavefront sensor 204.

The wavefront sensor 204 receives an imaging light beam containing the aberration information of the human eye and transmits the aberration information to the control module 10, the control module 10 performs wavefront calculation, detects wavefront aberration, obtains a wavefront control voltage and output the wavefront control voltage to the wavefront corrector 201, and the wavefront corrector 201 corrects the wavefront aberration.

Wherein, the beam scanning module 3 includes a first transmissive or reflective telescope 301, a biaxial scanning mirror 302 and a second transmissive or reflective telescope 303 arranged successively along the incident optical path. The biaxial scanning mirror 302 is driven by a periodic voltage outputted from the control module 10 to perform horizontal and vertical two-dimensional scanning of the retinal plane.

In a preferred embodiment, the biaxial scanning mirror 302 may be a two-dimensional scanning mirror for realizing the horizontal and vertical scanning of the light beam, or is a combination of two one-dimensional scanning mirrors wherein scanning directions of the two scanning mirrors are set to be orthogonal to each other for realizing horizontal scanning and vertical scanning of the light beam respectively, and the two scanning mirrors are connected by a transmissive telescope or a reflective telescope to achieve a matching of light pupils. In this embodiment, the biaxial scanning mirror 302 is a fast reflection mirror MR-30-15-G-25×25D available from Optotune Company.

In a preferred embodiment, the first transmissive or reflective telescope is used to connect the wavefront corrector 201 to the biaxial scanning mirror 302 to achieve a matching of light pupils, and has a magnification equal to a ratio of the light-transmitting aperture of the biaxial scanning mirror 302 to the light-transmitting aperture of the wavefront corrector 201; and the second transmissive or reflective telescope is used to conjugatively transmit the exiting light of the biaxial scanning mirror 302 to the first dichroic beam splitter 401, and has a magnification of $N_3$.

Wherein, the small field-of-view relay module 5 includes a transmissive telescope comprising a first lens 501 and a second lens 503 and having a magnification, marked as $N_5$, greater than 1, or a reflective telescope comprising a first spherical reflector 501 and a second spherical reflector 503 and having a magnification, marked as $N_5$, greater than 1. The small field-of-view relay module 5 further includes a first focusing mechanism 502 disposed between the two lenses or spherical reflectors of the telescope, wherein the first focusing mechanism 502 includes two orthogonal planar reflection mirrors and is configured to reciprocate along a central optical axis of the telescope to compensate for a refractive error of the human eye.

The large field-of-view relay module 6 includes a transmissive telescope comprising a third lens 601 and a fourth lens 603 and having a magnification, marked as $N_6$, less than 1, or a reflective telescope comprising a third spherical reflector 601 and a fourth spherical reflector 603 and having a magnification, marked as $N_6$, less than 1. The large field-of-view relay module 6 further includes a second focusing mechanism 602 disposed between the two lenses or spherical reflectors of the telescope, wherein the second focusing mechanism 602 includes two orthogonal planar reflection mirrors and is configured to reciprocate along a central optical axis of the telescope to compensate for a refractive error of the human eye.

The common beam scanning retinal imaging system further comprises a dichroic beam splitter module including a first dichroic beam splitter 401, a second dichroic beam splitter 402, a third dichroic beam splitter 403 and a fourth dichroic beam splitter 404 arranged successively along an incident optical path.

Wherein, the first dichroic beam splitter 401 has a reflection effect on the lights with the wavelengths $\lambda_1$ and $\lambda_4$, and has a transmission effect on the light with the wavelength $\lambda_2$; the second dichroic beam splitter 402 has a reflection effect on the light with the wavelength $\lambda_1$, and has a transmission effect on the lights with the wavelengths $\lambda_2$ and $\lambda_4$; the third dichroic beam splitter 403 has a reflection effect on the lights with the wavelengths $\lambda_2$ and $\lambda_3$, and has a transmission effect on the lights with the wavelengths $\lambda_1$ and $\lambda_4$; and the fourth dichroic beam splitter 404 has a reflection effect on the light with the wavelength $\lambda_2$ and has a transmission effect on the lights with the wavelengths $\lambda_1$, $\lambda_3$, and $\lambda_4$.

Wherein, the detection module 8 includes a fifth dichroic beam splitter 800, a first detection optical path and a second detection optical path. The fifth dichroic beam splitter 800 transmits one part of the received light to the first detection optical path and simultaneously reflects the other part of the received light to the second detection optical path. The first detection optical path includes a first collection lens 801, a first pinhole 802 and a first detector 803, and the second detection optical path includes a second collection lens 811, a second pinhole 812 and a second detector 813. One part of the returning imaging light beam carrying the light intensity information of the human eye is transmitted through the fifth dichroic beam splitter 800 and outputted to the first collection lens 801, passes through the first pinhole 802 and reaches the first detector 803, so as to obtain a retinal imaging image. The other part of the returning imaging light beam carrying the light intensity information of the human eye is reflected by the fifth dichroic beam splitter 800 and outputted to the second collection lens 811, passes through the second pinhole 812 and reaches the second detector 813, so as to obtain another retinal imaging image.

In a preferred embodiment, the fifth dichroic beam splitter 800 is configured to have a transmission effect on the light with the wavelength $\lambda_1$ and have a reflection effect on the light with the wavelength $\lambda_2$, or have a reflection effect on the light with the wavelength $\lambda_1$ and have a transmission effect on the light with the wavelength $\lambda_2$. The fifth dichroic beam splitter 800 is configured in either of the two settings, which does not affect the actual operating effect of the system. When the fifth dichroic beam splitter 800 is configured to have a transmission effect on the light with the wavelength $\lambda_1$, the corresponding light beam is transmitted thereby to enter the collection lens 801 and pinhole 802 to reach the detector 803; and when the fifth dichroic beam splitter 800 is configured to have a reflection effect on the light with the wavelength $\lambda_1$, the corresponding light beam is reflected thereby to enter the collection lens 811 and the ole 812 to reach the detector 813.

Further preferably, in this embodiment, the fifth dichroic beam splitter 800 is configured to have a transmission effect on the light with the wavelength $\lambda_1$, and the corresponding light beam is transmitted thereby to enter the collection lens 801 and the pinhole 802 to reach the detector 803, and the detector 803 converts the received light signal of the fundus retina into an electrical signal and outputs the electrical signal to the control module 10. The control module 10 performs signal synchronization processing, samples the electrical signal to reconstruct an imaging image of the retina with a small field of view and high resolution, which is outputted to the output module 11 by the control module 10 for performing functions such as display, storage, processing.

In a preferred embodiment, the collection lenses 801 and 811 may be an achromatic lens, an apochromatic lens or a combination of lenses, and have a focal length no less than 100 mm. The pinholes 802 and 812 have a size of 50 microns, which can also be changed according to the light energy efficiency while not exceeding 200 microns. The detectors 803 and 813 may be a photomultiplier tube, an avalanche diode, or a highly sensitive camera.

There are multiple processes in the actual work of the imaging system of the present application, including a small field-of-view high-resolution imaging process, a large field-of-view low-resolution imaging process, and subject-related processes. These will be further described below in conjunction with the embodiments.

1. Small field-of-view high-resolution imaging process is as following:

The light beam emitted by the light source module 1, having the wavelength $\lambda_1$ and approximated as emitted by a point light source 101, is collimated into a parallel light beam by the collimator 102. The parallel light beam is split by the first beam splitter 103, so that 20% of the parallel light beam is transmitted through the first beam splitter 103 and then reflected by the wavefront corrector 201. The transmitted parallel light beam continues to pass through the first transmissive or reflective telescope 301 to achieve a matching of light pupil apertures, and reaches the biaxial scanning mirror 302. The biaxial scanning mirror 302 scans the light beam horizontally and vertically, and the scanning light beam propagates through the second transmissive or reflective telescope 303, reaches the dichroic beam splitter 401, is reflected by the first dichroic beam splitter 401, and then goes through the small field-of-view relay module 5 to reach the second dichroic beam splitter 402. A badal focusing mechanism 502 composed of a set of planar reflection mirrors is arranged between the lens or spherical reflectors 501 and 503 that make up the small field-of-view relay module 5. The badal focusing mechanism 502 can reciprocate back and forth along a central optical axis to compensate for a refractive error of the human eye. The light beam is reflected by the second dichroic beam splitter 402, is transmitted through the third dichroic beam splitter 403 and the fourth dichroic beam splitter 404, passes through the hollow part of the ring-shaped LED array 701 to reach the human eye, and is focused on a point on the fundus retina by the optical system of the human eye.

The incident light beam is scattered by the fundus retina to form a scattered imaging light beam carrying aberration information of the human eye and light intensity information at the point on the fundus retina. The scattered imaging light beam returns along the original optical path and exits from the beam scanning module 3, and is then reflected by the wavefront corrector 201 to the first beam splitter 103. The first beam splitter 103 reflects 80% of the imaging light beam to the second beam splitter 202 for further light splitting, wherein 5% of the light reaching the second beam splitter 202 is reflected into the optical filter 203 and the wavefront sensor 204; and the remaining 95% of the light is transmitted to the fifth dichroic beam splitter 800.

The wavefront sensor 204 transmits the received aberration information of the human eye to the control module 10. The control module 10 restores the wavefront aberration and calculates an aberration correction voltage, and then transmits the aberration correction voltage to the wavefront corrector 201 for the wavefront corrector 201 to perform real-time correction of human eye aberration.

At the same time, in this embodiment, the fifth dichroic beam splitter 800 is configured to have a transmission effect on the light with the wavelength $\lambda_1$. The light is transmitted through the second beam splitter 202, and is then transmitted totally through the fifth dichroic beam splitter 800, then passes through the first collection lens 801 and the first pinhole 802, and finally reaches the first detector 803. The first detector 803 converts the received light signal of the fundus retina into an electrical signal and outputs the electrical signal to the control module 10. The control module 10 performs signal synchronization processing, samples the electrical signal to reconstruct an imaging image of the retina with a small field of view and high resolution, which is then displayed and stored by the output module 11.

Figure 3:
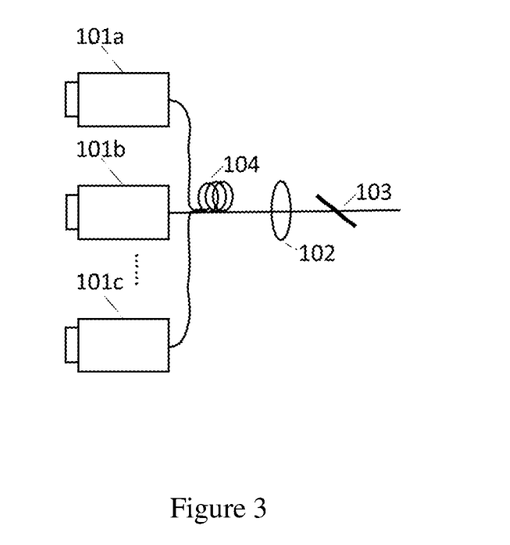
FIG. 3 is a diagram of an optical path structure of the light source module in an embodiment of the present application.
Figure 4:
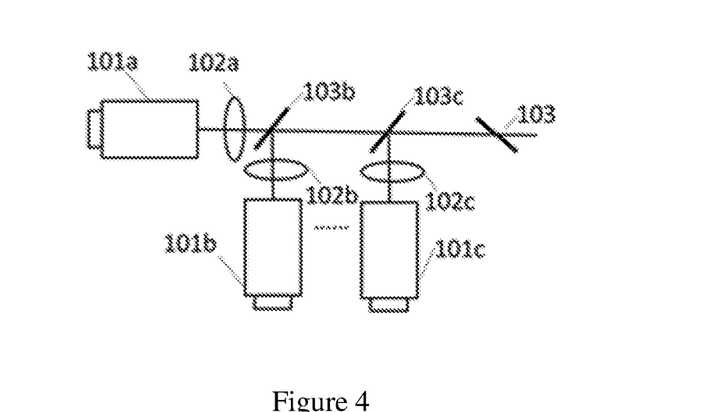
FIG. 4 is a diagram of an optical path structure of the light source module in another embodiment of the present application.

The light source 101 having the wavelength $\lambda_1$ at least includes one or more of laser light sources 101 with a characteristic wavelength within the range of 600 nm-850 nm. The lights emitted from multiple light sources 101 (101a, 101b, 101c) may be coupled by an optical-fiber coupler 104, go into a collimator 102 to be collimated into a parallel light beam, and enter the first beam splitter 103, as shown in FIG. 3. The lights emitted from multiple light sources 101 (101a, 101b, 101c) may also be collimated by corresponding collimators 102 (102a, 102b, 102c) respectively into parallel light beams which are then coupled by several beam splitters (103b, 103c) via transmitting or reflecting to enter the optical path, and are then coupled by the first beam splitter 103 to enter the optical path of the system, as shown in FIG. 4. Typical optional wavelengths are 670 nm, 730 nm, 795 nm, 830 nm, etc. Preferably, $\lambda_1$ selected in this embodiment as the small field-of-view high-resolution imaging wavelength includes 670 nm and 795 nm.

The optical filter 203 may be a broadband filter 203 whose transmission wavelength band satisfies the selected wavelength $\lambda_1$ for the small field-of-view high-resolution imaging, or is a combination of multiple narrowband filters whose combined transmission wavelength band satisfies the selected wavelength $\lambda_1$ for the small field-of-view high-resolution imaging.

The collimator 102 may be a single lens, an achromatic lens, an apochromatic lens, a combination of lenses or a parabolic mirror, and is used to collimate the light beam emitted by the light source 101 into a parallel light beam. The reflective collimator RC12FC-P01 available from Thorlabs Company is used in this embodiment.

The first beam splitter 103 is a broadband beam splitter with a transmittance-to-reflectance ratio of 20:80. The second beam splitter 202 is a broadband beam splitter with a transmittance-to-reflectance ratio of 95:5.

The biaxial scanning mirror 302 may be a two-dimensional scanning mirror for realizing the horizontal and vertical scanning of the light beam, or is a combination of two one-dimensional scanning mirrors wherein scanning directions of the two scanning mirrors are set to be orthogonal to each other for realizing horizontal scanning and vertical scanning of the light beam respectively, and the two scanning mirrors are connected by a transmissive telescope or a reflective telescope to achieve a matching of light pupils. Preferably, in this embodiment, the biaxial scanning mirror 302 is a fast reflection mirror MR-30-15-G-25×25D available from Optotune Company.

The small field-of-view relay module 5 includes a transmissive telescope comprising lenses 501 and 503 and having a magnification, marked as $N_5$, greater than 1, or a reflective telescope comprising spherical reflectors 501 and 503 and having a magnification, marked as $N_5$, greater than 1.

In this embodiment, in order to satisfy the small field-of-view high-resolution imaging function, the light beam with the wavelength $\lambda_1$ has a diameter of 6-8 mm at the pupil of the human eye. The product of magnifications of the two sets of telescopes, including the second transmissive or reflective telescope 303 and the transmissive or reflective telescope comprising the lenses or spherical reflectors 501, 503, is greater than 1 and is equal to a ratio of the diameter of the light beam with the wavelength $\lambda_1$ at the human eye pupil to the light-transmitting aperture of the biaxial scanning mirror 302. When the light-transmitting aperture of the biaxial scanning mirror 302 is 2 mm, the product of the magnifications $N_3$ and $N_5$ of the two sets of telescopes is 3-4; and when the light-transmitting aperture of the biaxial scanning mirror 302 is 3 mm, the product of the magnifications $N_3$ and $N_5$ of the two sets of telescopes is 2-3.

2. Large field-of-view low-resolution imaging process is as following:

The light beam emitted by the light source module 1, having the wavelength $\lambda_2$ and approximated as emitted by a point light source 101, is collimated into a parallel light beam by the collimator 102. The parallel light beam is split by the first beam splitter 103, so that 20% of the parallel light beam is transmitted through the first beam splitter 103 and then reflected by the wavefront corrector 201. The transmitted parallel light beam continues to pass through the first transmissive or reflective telescope 301 to achieve a matching of light pupil apertures, and reaches the biaxial scanning mirror 302. The biaxial scanning mirror 302 scans the light beam horizontally and vertically, and the scanning light beam propagates through the second transmissive or reflective telescope 303, reaches the dichroic beam splitter 401, is transmitted through the first dichroic beam splitter 401 and the second dichroic beam splitter 402, is then reflected by the third dichroic beam splitter 403, and then goes through the large field-of-view relay module 6 to reach the fourth dichroic beam splitter 404. A badal focusing mechanism 602 composed of a set of planar reflection mirrors is arranged between the lens or spherical reflectors 601 and 603 that make up the large field-of-view relay module 6. The badal focusing mechanism 602 can reciprocate back and forth along a central optical axis to compensate for a refractive error of the human eye. The light beam is reflected by the fourth dichroic beam splitter 404, passes directly through the hollow part of the ring-shaped LED array 701 to finally reach the human eye, and is focused on a point on the fundus retina by the optical system of the human eye.

The incident light beam is scattered by the fundus retina to form a scattered imaging light beam carrying light intensity information at the point on the fundus retina. The scattered imaging light beam returns along the original optical path and exits from the beam scanning module 3, and is then reflected by the wavefront corrector 201 to the first beam splitter 103. The first beam splitter 103 reflects 80% of the imaging light beam to the second beam splitter 202 for further light splitting, 95% of the light reaching the second beam splitter 202 is transmitted to the fifth dichroic beam splitter 800.

At the same time, in this embodiment, the fifth dichroic beam splitter 800 is configured to have a reflection effect on the light with the wavelength $\lambda_2$. The light is transmitted through the second beam splitter 202, and is then totally reflected by the fifth dichroic beam splitter 800, then passes through the second collection lens 811 and the second pinhole 812, and finally reaches the second detector 813. The second detector 813 converts the received light signal of the fundus retina into an electrical signal and outputs the electrical signal to the control module 10. The control module 10 performs signal synchronization processing, samples the electrical signal to reconstruct an imaging image of the retina with a large field of view and low resolution, which is then displayed and stored by the output module 11.

The light source 101 has the wavelength $\lambda_2$ which is a characteristic wavelength in the range of 900 nm-1000 nm. Typical optional wavelengths are 904 nm, 950 nm, etc. Preferably, $\lambda_2$ selected in this embodiment as the large field-of-view low-resolution imaging wavelength is 950 nm.

The large field-of-view relay module 6 includes a transmissive telescope comprising lenses 601 and 603 and having a magnification, marked as $N_6$, less than 1, or a reflective telescope comprising spherical reflectors 601 and 603 and having a magnification, marked as $N_6$, less than 1.

In this embodiment, in order to satisfy the large field-of-view low-resolution imaging function, the light beam with the wavelength $\lambda_2$ has a diameter of 1-3 mm at the pupil of the human eye 12. The product of magnifications of the two sets of telescopes, including the second transmissive or reflective telescope 303 and the transmissive or reflective telescope comprising the lenses or spherical reflectors 601, 603, is equal to a ratio of the diameter of the light beam with the wavelength $\lambda_2$ at the human eye pupil to the light-transmitting aperture of the biaxial scanning mirror 302. When the light-transmitting aperture of the biaxial scanning mirror 302 is 2 mm, the product of the magnifications $N_3$ and $N_6$ of the two sets of telescopes is 0.5-1.5; and when the light-transmitting aperture of the biaxial scanning mirror 302 is 3 mm, the product of the magnifications $N_3$ and $N_6$ of the two sets of telescopes is 1/3-1.

3. Subject-related processes

The subject-related processes mainly include alignment and monitoring of the pupil, and guidance and fixation of the sight beacon.

(1) Alignment and monitoring of the pupil

The pupil monitoring module 7 includes a ring-shaped LED array 701, an imaging lens 702, and an area-array detector 703. The ring-shaped LED array 701 includes at least three LED beads arranged along a ring at equal intervals, the hollow part of the ring-shaped LED array has a light-transmitting aperture no less than the diameter of the imaging light beam. Light with the wavelength $\lambda_3$ is emitted by the ring-shaped LED array 701 to reach the human eye pupil, and is reflected by the human eye pupil to obtain a reflected light beam. The reflected light beam goes through the hollow part of the ring-shaped LED array 701, is transmitted through the fourth dichroic beam splitter 404, is reflected by the third dichroic beam splitter 403, and is focused on the area-array detector 703 by the imaging lens 702. The area-array detector 703 converts the light signal into an electrical signal, and outputs the electrical signal to the control module 10 to obtain a pupil imaging image, and outputs the pupil imaging image to the output module 11 for performing functions such as display, storage, processing.

When the system of the present application works, the subject's head is placed on a headrest. The headrest has a three-dimensional translation adjustment function, can be adjusted manually via a guide rail or can be configured to be adjusted automatically via a guide rail driven by a motor that is driven by the control module 10, so as to make the pupil imaged in a central area of the field of view.

The LED beads of the ring-shaped LED array 701 are selected to have a characteristic wavelength $\lambda_3$ in the wavelength range above 1000 nm, and typical optional wavelengths are 1020 nm and 1310 nm. Preferably, the wavelength is selected to be 1020 nm in this embodiment.

(2) Guidance and fixation of the sight beacon

The sight beacon module 9 includes the LED array 901, the sight beacon lens 902, and the first planar reflection mirror 903. An LED bead in the LED array 901 is lit by the control module 10, and emits light with the wavelength $\lambda_4$ which propagates through the sight beacon lens 902, is reflected by the first planar reflection mirror 903, is reflected by the first dichroic beam splitter 401, is sequentially transmitted through the second, third, and fourth dichroic beam splitters 402, 403, 404, passes through the hollow part of the ring-shaped LED array 701, and finally reaches the human eye 12, so as to allow the human eye to gaze at the luminous LED bead to achieve sight fixation.

The beads located at different positions of the LED array 901 are lit by the control module 10, so as to allow different areas of the fundus retina to be guided as the imaging area.

The LED array 901 includes LED beads arranged in an equally spaced array, which is typically 3×3, 4×4, etc. The selected wavelength is a certain characteristic wavelength $\lambda_4$ in the visible light band, and maintains a bandwidth difference of at least 50 nm from the wavelengths $\lambda_1$ and $\lambda_2$ included in the light source 101. In this embodiment, the wavelength $\lambda_4$ is 550 nm.

Figure 5:
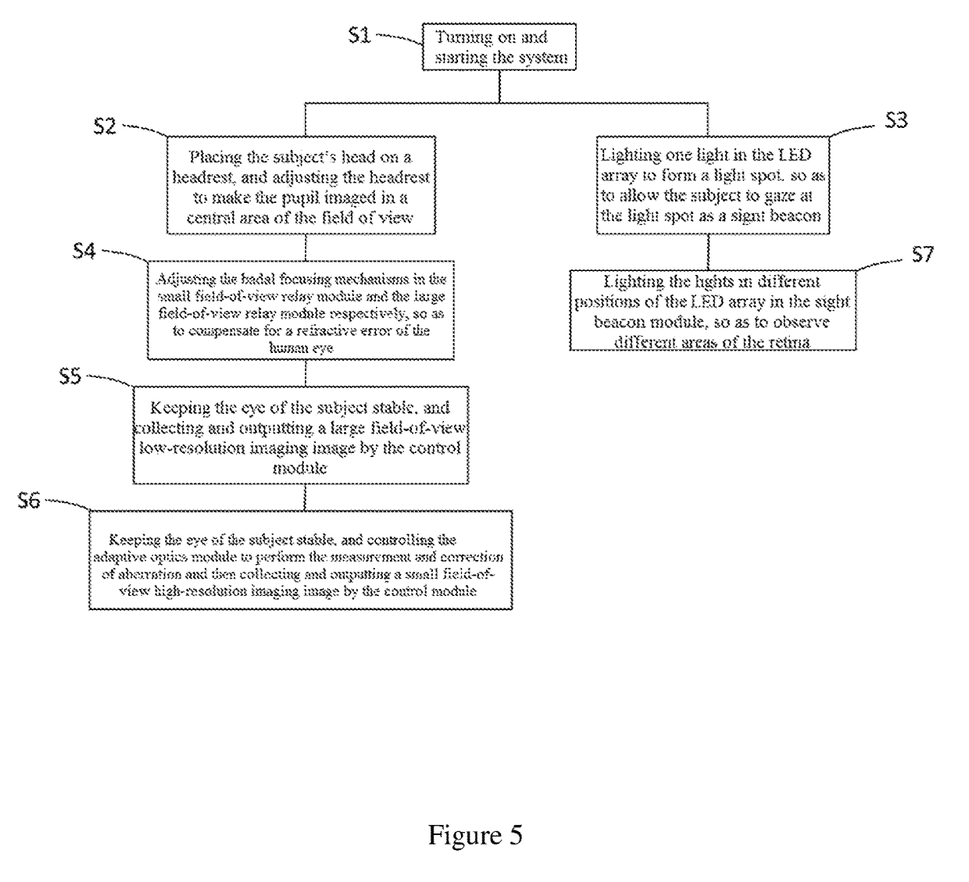
FIG. 5 is a flow chart of an imaging process of the common beam scanning retinal imaging system of the present application.

The specific operation flow of the imaging method of the common beam scanning retinal imaging system of the present application comprises the following steps, as shown FIG. 5:

(1) Turning on and starting the system.
(2) Placing the subject's head on the headrest and turning on the pupil monitoring module 7; adjusting the headrest manually or automatically by the control module 10 to make it translate three-dimensionally, so that the pupil is imaged in a central area of the field of view;
(3) Lighting one light in the LED array 901 to form a light spot, so as to allow the subject to gaze at the light spot to achieve sight fixation;

(4) Adjusting the badal focusing mechanisms 502 and 602 in the small field-of-view relay module 5 and large field-of-view relay module 6 respectively, so as to compensate for a refractive error of the human eye;

(5) Keeping the eye of the subject stable, and collecting and outputting a large field-of-view low-resolution imaging image by the control module 10;

(6) Keeping the eye of the subject stable, and controlling the adaptive optics module 2 to perform the measurement and correction of aberration and then collecting and outputting a small field-of-view high-resolution imaging image by the control module 10;

(7) Lighting the lights in different positions of the LED array 901, repeating step (5) and step (6) to collect a large field-of-view low-resolution images and small field-of-view high-resolution images in different areas of the retina;

The operations of step (5) and step (6) are selectable to be performed without requirement of a particular sequential relation.

As compared with domestic and foreign technological achievements in the field of confocal scanning laser imaging, the present application provides a common beam scanning retinal imaging system based on the basic principles of confocal scanning technology. The system of the present application can perform real-time correction of human eye aberration by adaptive optics technology, and realize the confocal scanning imaging function in a large field of view with a single-time large field-of-view imaging range of greater than 20 degrees and the adaptive optics high-resolution imaging function in a small field of view with a single-time small field-of-view imaging range of no more than 5 degrees simultaneously by the common beam synchronous scanning configuration combined with the two relay optical path structures for both the small field of view and the large field of view. The system can not only observe disease lesions in a wide range on the retina by the large field-of-view imaging, but also observe the fine structures of the lesions by the small field-of-view high-resolution imaging, which greatly expands the application range of the existing confocal imaging equipment.

The common beam scanning retinal imaging system of the present application can simultaneously obtain large field-of-view low-resolution imaging images and small field-of-view high-resolution imaging images of the fundus retina by using only one set of scanning mechanism and the common optical path structure. The two types of imaging images are completely synchronous, and have the same center position and imaging speed. The system realizes the coupling and separation of different imaging beams in a common optical path by means of two separate sets of relay transition optical paths, and simultaneously performs illumination and imaging detection of the fundus retina. The system has a simple structure, simple control and rich functions. In addition, the system is also equipped with a sight beacon module. When the human eye gazes at the sight beacons in different positions and the different areas of the fundus retina are illuminated by the light beam successively, large field-of-view low-resolution imaging images and small field-of-view high-resolution imaging images of each area of the retina are obtained.

The common beam scanning retinal imaging system of the present application can simultaneously obtain large field-of-view low-resolution imaging images and small field-of-view high-resolution imaging images of the fundus retina. The two types of imaging images are collected by a common optical path structure. Therefore, the two types of imaging images have the same center position and imaging speed, and the image characteristics thereof have good consistency, which is convenient for comparison processing and operation. At the same time, the system has a simple structure, and high-resolution and low-resolution retinal imaging images can be simultaneously acquired by the common optical path structure: characteristics of the structure and lesions over a large area on the retina can be observed by the large field-of-view low-resolution imaging images, and fine structures of the respective areas, such as cells, capillaries, nerve fibers, etc., can be observed by the small field-of-view high-resolution imaging images. A variety of imaging images are acquired by common path optical beam scanning to meet the needs of different application scenes, which greatly expands the application range of the retinal imaging.

Although the embodiments of the present application have been disclosed above, they are not limited to the applications listed in the specification and embodiments, and may be applied to various fields suitable for the present application. For a person skilled in the art, additional modifications can be easily implemented, so the present application is not limited to specific details, without departing from the general concept defined by the claims and equivalent scope thereof.

What is claimed is:

1. A common beam scanning retinal imaging system, characterized in that, the system comprises: a light source module, an adaptive optics module, a beam scanning module, a small field-of-view relay module, a large field-of-view relay module, a sight beacon module, a pupil monitoring module, a detection module, a control module and an output module;

the light source module is configured to emit a parallel light beam with at least two different wavelengths, wherein the parallel light beam irradiates a human eye after going through the adaptive optics module, the beam scanning module, and the small field-of-view relay module or the large field-of-view relay module sequentially, imaging light that is scattered by the human eye and carries aberration information of the human eye and light intensity information returns along an original optical path of the parallel light beam and reaches the adaptive optics module and the detection module;

the adaptive optics module is configured to receive the imaging light carrying the aberration information of the human eye, and perform real-time measurement and correction of wavefront aberration;

the beam scanning module includes a biaxial scanning mirror which is connected to the adaptive optics module through a first transmissive or reflective telescope along an incident end of the optical path and is connected to the small field-of-view relay module or the large field-of-view relay module through a second transmissive or reflective telescope along an exit end of the optical path, so as to achieve a small field-of-view high-resolution imaging and a large field-of-view low-resolution imaging, respectively;

the small field-of-view relay module is configured as a beam expanding telescope, and the large field-of-view relay module is configured as a beam contracting telescope;

the sight beacon module is configured to guide and fix a sight beacon of the human eye;

the pupil monitoring module is configured to align and monitor a pupil of the human eye;

the detection module is configured to receive the returning imaging light of the human eye, convert the imaging light into an electrical signal, and transmit the electrical signal to the control module; and the output module is configured to connect to the control module, and display and store imaging images of the human eye;

wherein the system further comprises a dichroic beam splitter module including a first dichroic beam splitter, a second dichroic beam splitter, a third dichroic beam splitter and a fourth dichroic beam splitter arranged successively along an incident optical path;

the light source module includes a light source, a collimator and a first beam splitter arranged successively along the incident optical path, and is configured to output a parallel light beam to the adaptive optics module, wherein the light emitted by the light source passes through the collimator, and is then partially transmitted through the first beam splitter to enter the adaptive optics module;

the adaptive optics module includes a wavefront corrector, a second beam splitter, an optical filter and a wavefront sensor arranged successively along a returning optical path of human eye imaging, and is connected to the beam scanning module; wherein the parallel light beam outputted by the light source module is reflected to the beam scanning module by the wavefront corrector; wherein the returning imaging light carrying the aberration information of the human eye and the light intensity information exits from the beam scanning module and is reflected to the first beam splitter by the wavefront corrector, one part of the light reflected by the first beam splitter is then reflected by the second beam splitter, passes through the optical filter, and then reaches the wavefront sensor, so as to realize measurement of wavefront aberration, and the other part of the light reflected by the first beam splitter is transmitted through the second beam splitter and enters the detection module; and the wavefront sensor is configured to receive an imaging light beam containing the aberration information of the human eye and transmit the aberration information to the control module, the control module is configured to perform wavefront calculation, detect wavefront aberration, obtain a wavefront control voltage and output the wavefront control voltage to the wavefront corrector, and the wavefront corrector is configured to correct the wavefront aberration.

2. The common beam scanning retinal imaging system according to claim 1, characterized in that, the detection module includes a fifth dichroic beam splitter, a first detection optical path and a second detection optical path, wherein the fifth dichroic beam splitter is configured to transmit one part of the received light to the first detection optical path and simultaneously reflect the other part of the received light to the second detection optical path; the first detection optical path includes a first collection lens, a first pinhole and a first detector, and the second detection optical path includes a second collection lens, a second pinhole and a second detector; wherein one part of the returning imaging light beam carrying the light intensity information of the human eye is transmitted through the fifth dichroic beam splitter and outputted to the first collection lens, passes through the first pinhole and reaches the first detector, so as to obtain a retinal imaging image; wherein the other part of the returning imaging light beam carrying the light intensity information of the human eye is reflected by the fifth dichroic beam splitter and outputted to the second collection lens, passes through the second pinhole and reaches the second detector, so as to obtain another retinal imaging image;

the beam scanning module includes a first transmissive or reflective telescope, a biaxial scanning mirror and a second transmissive or reflective telescope arranged successively along the incident optical path, wherein the biaxial scanning mirror is configured to be driven by a periodic voltage outputted from the control module to perform horizontal and vertical two-dimensional scanning of the retinal plane.

3. The common beam scanning retinal imaging system according to claim 2, characterized in that, the sight beacon module includes an LED array, a sight beacon lens, and a first planar reflection mirror, wherein the light emitted by any one of LED beads in the LED array after being lit by the control module propagates through the sight beacon lens, is reflected by the first planar reflection mirror, is reflected by the first dichroic beam splitter, and is sequentially transmitted through the second dichroic beam splitter, the third dichroic beam splitter and the fourth dichroic beam splitter, and then reaches the human eye, so as to allow the human eye to gaze at the luminous LED bead to achieve sight fixation;

the pupil monitoring module includes a ring-shaped LED array, an imaging lens, and an area-array detector, wherein the light emitted by the ring-shaped LED array illuminates the pupil of the human eye, and is reflected by the pupil of the human eye, passes through a hollow part of the ring-shaped LED array, is transmitted through the fourth dichroic beam splitter, is reflected by the third dichroic beam splitter, and is finally focused by the imaging lens to the area-array detector for pupil imaging; and the area-array detector is configured to convert the received light signal into an electrical signal and then output the electrical signal to the control module; the control module is configured to obtain a pupil imaging image and finally output the pupil imaging image to the output module for display and storage.

4. The common beam scanning retinal imaging system according to claim 3, characterized in that, the small field-of-view relay module includes a transmissive telescope comprising a first lens and a second lens and having a magnification greater than 1, or a reflective telescope comprising a first spherical reflector and a second spherical reflector and having a magnification greater than 1; the small field-of-view relay module further includes a first focusing mechanism disposed between the two lenses or spherical reflectors of the telescope, wherein the first focusing mechanism includes two orthogonal planar reflection mirrors and is configured to reciprocate along a central optical axis of the telescope to compensate for a refractive error of the human eye;

the large field-of-view relay module includes a transmissive telescope comprising a third lens and a fourth lens and having a magnification less than 1, or a reflective telescope comprising a third spherical reflector and a fourth spherical reflector and having a magnification less than 1; the large field-of-view relay module further includes a second focusing mechanism disposed between the two lenses or spherical reflectors of the telescope, wherein the second focusing mechanism includes two orthogonal planar reflection mirrors and is configured to reciprocate along a central optical axis of the telescope to compensate for a refractive error of the human eye.

5. The common beam scanning retinal imaging system according to claim 4, characterized in that, the small field-of-view high-resolution imaging is performed by the following process:

the light beam emitted by the light source module goes through the wavefront corrector of the adaptive optics module and the beam scanning module, and is reflected by the first dichroic beam splitter to enter the small field-of-view relay module, then exits from the small field-of-view relay module and is reflected by the second dichroic beam splitter, is transmitted through the third dichroic beam splitter and the fourth dichroic beam splitter, passes through the hollow part of the ring-shaped LED array to reach the human eye, and is focused on a point on the fundus retina by the optical system of the human eye; the incident light beam is scattered by the fundus retina to form a scattered imaging light beam carrying aberration information of the human eye and light intensity information at the point on the fundus retina; the scattered imaging light beam returns along the original optical path and exits from the beam scanning module, and is then reflected by the wavefront corrector to the first beam splitter; the first beam splitter reflects the light beam to the second beam splitter, one part of the light reflected by the first beam splitter is reflected by the second beam splitter to enter the wavefront sensor; the wavefront sensor transmits the received aberration information of the human eye to the control module; the control module restores the wavefront aberration and calculates an aberration correction voltage, and then transmits the aberration correction voltage to the wavefront corrector to perform real-time correction of human eye aberration; at the same time, the other part of the light reflected by the first beam splitter is transmitted through the second beam splitter, and is then transmitted totally through the fifth dichroic beam splitter, then passes through the first collection lens and the first pinhole, and finally reaches the first detector; the first detector converts the received light signal of the fundus retina into an electrical signal and outputs the electrical signal to the control module; the control module performs signal synchronization processing, samples the electrical signal to reconstruct an imaging image of the retina with a small field of view and high resolution, which is then displayed and stored by the output module; and the large field-of-view low-resolution imaging is performed by the following process:

the light beam emitted by the light source module goes through the wavefront corrector of the adaptive optics module and the beam scanning module, is transmitted through the first dichroic beam splitter and the second dichroic beam splitter, and is reflected by the third dichroic beam splitter to enter the large field-of-view relay module, then exits from the large field-of-view relay module and is reflected by the fourth dichroic beam splitter, passes through the hollow part of the ring-shaped LED array to reach the human eye, and is focused on a point on the fundus retina by the optical system of the human eye; the incident light beam is scattered by the fundus retina to form a scattered imaging light beam carrying light intensity information at the point on the fundus retina; the scattered imaging light beam returns along the original optical path and exits from the beam scanning module, and is then reflected by the wavefront corrector to the first beam splitter; the first beam splitter reflects the light beam to the second beam splitter, the light reflected by the first beam splitter is transmitted through the second beam splitter, and is then reflected totally by the fifth dichroic beam splitter, then passes through the second collection lens and the second pinhole, and finally reaches the second detector; the second detector converts the received light signal of the fundus retina into an electrical signal and output the electrical signal to the control module; the control module performs signal synchronization processing, samples the electrical signal to reconstruct an imaging image of the retina with a large field of view and low resolution, which is then displayed and stored by the output module.

6. The common beam scanning retinal imaging system according to claim 5, characterized in that, the light source module includes at least two light sources, wherein the lights emitted from the at least two light sources are coupled by an optical-fiber coupler and go into a collimator to be collimated into a parallel light beam, or wherein the lights emitted from the at least two light sources are collimated by corresponding collimators respectively into parallel light beams which are then combined by a dichroic beam splitter to enter the optical path;

the light emitted by the light source module includes light with a wavelength Xi of 600 nm-850 nm and light with a wavelength $\lambda_2$ of 900 nm-1000 nm, wherein the light with the wavelength $\lambda_1$ is used for the small field-of-view high-resolution imaging, and the light with the wavelength $\lambda_2$ is used for the large field-of-view low-resolution imaging;

the ring-shaped LED array includes at least three LED beads arranged along a ring at equal intervals, the hollow part of the ring-shaped LED array has a light-transmitting aperture no less than the diameter of the imaging light beam; the wavelength of the light emitted by the LED beads is $\lambda_3$ which is greater than 1000 nm;

the LED array of the sight beacon module includes LED beads arranged in an equally spaced array and emitting light with a wavelength $\lambda_4$ in a range of 380 nm-760 nm in the visible light band, and the difference between $\lambda_4$ and either of $\lambda_1$, $\lambda_2$ is at least 50 nm.

7. The common beam scanning retinal imaging system according to claim 6, characterized in that, the first dichroic beam splitter has a reflection effect on the lights with the wavelengths $\lambda_1$ and $\lambda_4$, and has a transmission effect on the light with the wavelength $\lambda_2$;

the second dichroic beam splitter has a reflection effect on the light with the wavelength $\lambda_1$, and has a transmission effect on the lights with the wavelengths $\lambda_2$ and $\lambda_4$;

the third dichroic beam splitter has a reflection effect on the lights with the wavelengths $\lambda_2$ and $\lambda_3$, and has a transmission effect on the lights with the wavelengths $\lambda_1$ and $\lambda_4$; and the fourth dichroic beam splitter has a reflection effect on the light with the wavelength $\lambda_2$ and has a transmission effect on the lights with the wavelengths $\lambda_1$, $\lambda_3$, and $\lambda_4$.

8. The common beam scanning retinal imaging system according to claim 5, characterized in that, the wavefront sensor in the adaptive optics module is selected from a microprism array Hartmann wavefront sensor, a microlens array Hartmann wavefront sensor, a quadrangular pyramid sensor and a curvature sensor; and the wavefront corrector is selected from a deformable reflection mirror, a liquid crystal spatial light modulator, a micromachined membrane deformable mirror, a micro-electromechanical deformable mirror, a double piezoelectric ceramic deformable mirror and a liquid deformable mirror;

the second dichroic beam splitter splits the imaging light beam reflected from the first beam splitter by reflecting 5% of the light to pass through the optical filter and enter the wavefront sensor for wavefront aberration measurement and transmitting the remaining 95% of the light to the fifth dichroic beam splitter;

the optical filter is a broadband filter whose transmission wavelength band satisfies the selected wavelength $\lambda_1$ for the small field-of-view high-resolution imaging, or is a combination of multiple narrowband filters whose combined transmission wavelength band satisfies the selected wavelength $\lambda_1$ for the small field-of-view high-resolution imaging; and wherein the imaging light beam with the selected wavelength $\lambda_2$ for the large field-of-view low-resolution imaging is completely blocked by the optical filter and does not enter the wavefront sensor;

the wavefront aberration detected by the wavefront sensor is processed by the control module, and the obtained wavefront control voltage is outputted to the wavefront corrector, so as to correct the wavefront aberration.

9. The common beam scanning retinal imaging system according to claim 5, characterized in that, the biaxial scanning mirror is a two-dimensional scanning mirror for realizing the horizontal and vertical scanning of the light beam, or is a combination of two one-dimensional scanning mirrors wherein scanning directions of the two scanning mirrors are set to be orthogonal to each other for realizing horizontal scanning and vertical scanning of the light beam respectively, and the two scanning mirrors are connected by a transmissive telescope or a reflective telescope to achieve a matching of light pupils;

the first transmissive or reflective telescope is configured to connect the wavefront corrector to the biaxial scanning mirror to achieve a matching of light pupils, and has a magnification equal to a ratio of the light-transmitting aperture of the biaxial scanning mirror to the light-transmitting aperture of the wavefront corrector; and the second transmissive or reflective telescope is configured to conjugatively transmit the exiting light of the biaxial scanning mirror to the first dichroic beam splitter.

\* \* \* \* \*